United States Patent
Levi et al.

(10) Patent No.: US 6,387,648 B1
(45) Date of Patent: May 14, 2002

(54) METHOD FOR ADJUSTING AND DISINFECTING LIQUIDS

(75) Inventors: Yves Levi, Verrieres le Buisson; Danièle Touati, Paris; Sam Dukan, Marseille, all of (FR)

(73) Assignee: Suez Lyonnaise des Eaux, Paris (FR)

( * ) Notice: Subject to any disclaimer, the term of this patent is extended or adjusted under 35 U.S.C. 154(b) by 0 days.

(21) Appl. No.: 09/508,964

(22) PCT Filed: Sep. 23, 1998

(86) PCT No.: PCT/FR98/02045

§ 371 Date: Jul. 17, 2000

§ 102(e) Date: Jul. 17, 2000

(87) PCT Pub. No.: WO99/16896

PCT Pub. Date: Apr. 8, 1999

(30) Foreign Application Priority Data

Sep. 28, 1997 (FR) .............................. 97 12082

(51) Int. Cl.[7] .............................. C12Q 1/32; C12Q 1/30; C12Q 1/34
(52) U.S. Cl. .............................. 435/26; 435/27; 435/28; 435/18
(58) Field of Search .............................. 435/26, 27, 25, 435/28, 18

(56) References Cited

U.S. PATENT DOCUMENTS

| | | | |
|---|---|---|---|
| 4,084,747 A | * 4/1978 | Alliger | 424/65 |
| 5,158,973 A | 10/1992 | Whitekettle et al. | 435/18 |
| 5,223,401 A | 6/1993 | Foltz et al. | 435/18 |
| 5,223,402 A | 6/1993 | Abbas et al. | 435/18 |
| 5,366,872 A | 11/1994 | Hird et al. | 435/4 |
| 5,397,473 A | * 3/1995 | Jewwll | 210/610 |

FOREIGN PATENT DOCUMENTS

| | | |
|---|---|---|
| EP | 0 574 977 | 12/1993 |
| FR | 2638170 | 4/1990 |
| JP | 10-243798 | 9/1998 |
| WO | WO 95/08639 | 3/1995 |

OTHER PUBLICATIONS

Stretton, R.J., and Manson,T.W., "Some Aspects of the Mode of Action of the Antibacterial Compound Bronopol (2–bromo–2–nirtopropan–1,3–diol)," *Journal of Applied Bacteriology*, vol. 36, No. 1, Mar. 1973, pp. 61–76.

* cited by examiner

*Primary Examiner*—Louise N. Leary
(74) *Attorney, Agent, or Firm*—Connolly Bove Lodge & Hutz LLP

(57) ABSTRACT

A Method for regulating the disinfection of a liquid includes a number of stages. At one stage of the said disinfection (stage 2), the activity of at least one enzyme is measured by bringing the microorganisms which may be present in the liquid into contact with a substrate capable of revealing the activity of the enzyme, this enzymatic activity being referred to as specific activity. At another stage (stage 1), prior to stage 2, there occurs measuring the activity of the same enzymes. This activity being referred to as initial activity. The next stage involves translating, for each enzyme, the specific activity and initial activity, into levels of microorganisms surviving in the liquid at stage 2 of the disinfection by means of a reference system pre-established with the aid of a sample of the liquid collected at stage 1 and then exposed to increasing doses of disinfectant. Then there is the next stage for adjusting, as a function of the level of surviving microorganisms, the nature and/or doses of physical or chemical agent(s) used for disinfection.

20 Claims, 3 Drawing Sheets

METHOD FOR ADJUSTING AND DISINFECTING LIQUIDS

FIELD OF THE INVENTION

The present invention relates, in a general manner, to means for regulating the disinfection of liquids. It relates more particularly to means of regulation using the measurement of enzymatic activities.

BACKGROUND OF THE INVENTION

The assurance of the quality and safety of animals, such as water intended for consumption, dietary liquid, bathing water, water intended for pharmaceutical or biotechnological preparations, depends directly on the reliability and the sensitivity of the techniques used in measure the number of microorganisms surviving in the said liquid.

The methods currently used for regulating the disinfection of a liquid use the techniques for culturing on agar and/or microscopy techniques.

The techniques for culturing on agar consist in counting the number of bacterial colonies which develop on various standardized nutrient agar media [e.g. French Standard NF T 90-414, Essais des Eaux, Recherche et dénombrement des coliformes et des coliformes thermotolérants (Water analysis, Identification and Enumeration of coliforms and of thermotolerant coliforms)]. These techniques have several disadvantages.

In the first instance, there may be mentioned the fact that they give their results only after 24 hours on average, which delays by as much the possible adjustment of the disinfection method.

The techniques for culturing on agar necessitates, furthermore, the carrying out of series of microbiological cultures for the analysis of each liquid sample. Indeed, all the microbial, and in particular bacterial, families do not develop on the same nutrient medium; thus, it is possible to detect no coliform after culturing on the standardized nutrient medium for the detection of coliforms, but to find a good number of other bacteria after culturing on other nutrient media. The choice of the nutrient agar media therefore determines the quality of the analysis. This choice is all the more delicate since a larger number of colonies has sometimes been observed after culturing on a medium other than the standardized nutrient medium for the detection of these same colonies. It has, for example, been demonstrated that the counts of the viable aerobic bacterial flora were higher on R2A agar medium than on the corresponding standardized nutrient medium (see for example <<A new rapid medium for enumeration and subculture of bacteria from potable water>> by Reasoner D. J. and Godreich E. F., App. Environm. Microbiol. (1985) 49-p.1–7). To establish a reliable negative diagnosis, the techniques for culturing on agar therefore require a multiplication of the analyses. The techniques for culturing on agar furthermore do not easily allow the regulation of the method of disinfection to be automated.

Bacteria are furthermore capable, and in particular following an environmental stress such as the application of a disinfection method, of adopting a form of resistance in which they no longer multiply while providing a minimal metabolism; as soon as more favourable environmental conditions are restored, these bacteria could resume their multiplication. Such bacteria are said to be <<non-culturable but viable>>: they are not detectable by the conventional techniques for culturing on agar and can represent a biological risk for the consumer.

A method which is currently available for controlling with virtual certainty the efficiency of the disinfection of a liquid uses microscopy techniques combined with specific staining. This method allows discrimination between culturable bacteria, non-culturable but viable bacteria and dead bacteria. It requires nevertheless the use of several staining tests for each sample and is technically difficult to automate.

SUMMARY OF THE INVENTION

The present invention aims to overcome the disadvantages of the prior art techniques and proposes a method for regulating the disinfection of a liquid, characterized in that it comprises:

A. at one stage of the said disinfection, designated hereinafter stage 2, measuring the activity of at least one enzyme by bringing the microorganisms which may be present in the said liquid into contact with a substrate chosen as being capable of revealing the activity of this or these enzyme(s), in particular by the conversion of the said substrate to coloured fluorescent or luminescent compounds or by the disappearance of the said substrate, this enzymatic activity being called hereinafter specific activity, B. at one stage, designated hereinafter stage 1, prior to the said stage 2, measuring the activity of the same enzyme (s) as in A, this activity being designated hereinafter initial activity, C. translating, for each enzyme, the said specific activity and initial activity, into levels of surviving microorganisms in the said liquid at stage 2 of the said disinfection by means of a reference system preestablished with the aid of a sample of the said liquid collected at the said stage 1 and then exposed to increasing doses of disinfectant(s), as well as D. adjusting, as a function of the said level of surviving microorganisms, of the nature and/or doses of physical or chemical agent(s) used for the said disinfection.

The expression surviving microorganisms is understood to mean in the present application culturable microorganisms and/or non-culturable but viable microorganisms.

The expression level of surviving microorganisms is understood to mean in the present application the ratio between the concentration of surviving microorganisms in the said liquid at the said stage 2 of a disinfection and the concentration of surviving microorganisms in the same liquid at the said stage 1. This level of surviving microorganisms is preferably expressed as reduction values in the form of negative powers of 10, or as log reduction which corresponds to $-\log_{10}$ (reduction).

The said stage 1 may, for example, correspond to a stage <<before disinfection>> of the said liquid and the said stage 2 to any stage of the disinfection method (stages <<after disinfection>> of the said liquid included).

The method according to the invention relates to liquids in which the microorganisms which may be present are subjected to very specific conditions, namely disinfection conditions, which induce notable stress of the cells.

The method for regulating the disinfection of a liquid according to the invention relates particularly to liquids intended to be brought into contact with humans or animals, whether through simple contact, absorption, ingestion, instillation or injection. It applies particularly to liquids intended to be in contact with humans or animals, such as bathing water, water intended for consumption, water intended for pharmaceutical or biotechnological preparations, or a dietary liquid.

The said bringing of the microorganisms which may be present in the said liquid into contact with the said substrate may be carried out by bringing the said liquid or a sample of the said liquid directly into contact with the said substrate, or alternatively by bringing a concentrate of the said microorganisms which may be present, such as a filtrate or a centrifugation pellet of the said liquid or liquid sample, into contact with the said substrate.

Prior to the measurement of the activity of some enzymes such as glucose-6-phosphate dehydrogenase or glutathione reductase, the method according to the invention advantageously comprises the step of subjecting the said liquid, liquid sample or concentration to a lysis treatment, especially by sonication.

Prior to the measurement of the activity of other enzymes such as catalase or superoxide dismutase, the preliminary lysis stage may be avoided: the activity of these enzymes may be measured with the aid of a substrate which diffuses into the microorganisms, such as lucigenin or hydrogen peroxide.

According to an advantageous aspect of the invention, the enzyme(s) whose activity or activities is (are) measured exhibit(s) in the said liquid, liquid sample or concentrate a ratio between the specific activity and the initial activity in close relationship, and with a slope which is significantly different from zero, preferably less than −0.2, with the level of surviving microorganisms over at least one zone of values of the said levels of surviving microorganisms. This is for example the case for glucose-6-phosphate dehydrogenase for log reduction values of between 0 and 3 approximately, for glutathion reductase for log reduction values of between 4 and 7 approximately, and for superoxide dismutase for log reduction values of between 3 and 6 approximately.

Other enzymes of interest may in particular form part of the family of dehydrogenases or the family of enzymes involved in the response to oxidative stress.

To determine if one or more enzymes are appropriate for carrying out the method of regulation according to the invention on a given liquid, the method may be carried out as follows:

collection of at least one sample of the said liquid and measurement of the concentration of surviving microorganisms (culturable microorganisms and/or non-culturable but viable microorganisms), in particular by culturing on agar and/or by staining and observations on a microscope, assay of the activity of each candidate enzyme on this or these liquid sample(s), exposure of the said liquid sample(s) to various doses of disinfectant(s) under conditions which are moreover equivalent (e.g. temperature and duration of exposure conditions), measurement of the activity of each candidate enzyme after exposure to various doses of disinfectant(s), plotting, for each candidate enzyme, of a curve showing the percentage of activity (enzyme activity, measured after exposure to the various doses of disinfectant(s), expressed relative to the corresponding enzymatic activity before exposure) as a function of the measured log reduction values (as defined above), determination, for each candidate enzyme, of the log reduction zone for which the slope of the said curve is significantly different from zero, preferably less than −0.2, this zone constituting the range of response of the candidate enzyme considered on the said liquid, a candidate enzyme is appropriate for carrying out the method according to the invention on the said liquid if its range of response comprises the log reduction values corresponding to the disinfection objectives aimed at for the liquid considered.

According to a particularly advantageous aspect of the invention, the or at least one of the enzyme(s) whose activity or activities is (are) measured is a glucose-6-phosphate dehydrogenase, a malate dehydrogenase, a glyceraldehyde-3-phosphate dehydrogenase, a catalase, a superoxide dismutase or a glutathion reductase. The said (or at least one of the said) enzymatic activity or activities is (are) then measured by converting a substrate and, where appropriate, in the presence of a cofactor, such as respectively glucose-6-phosphate and cofactor NADP, L-malate and cofactor NAD, glyceraldehyde-3-phosphate and cofactor NAD, lucigenin, hydrogen peroxide, oxidized glutathion and cofactor NADPH.

According to an advantageous embodiment of the invention, the said measurements of specific activity and of initial activity are made with the aid of an apparatus for detecting light intensity such as a spectrophotometer, spectrofluorometer or a luminometer, optionally having several channels for analysis.

According to another advantageous embodiment of the invention, the said translation into level of surviving microorganisms with the aid of the said preestablished reference system comprises for each enzyme, the calculation of the ratio between the specific activity and initial activity, optionally expressed as a percentage.

According to yet another advantageous embodiment of the invention, the said reference system exists in graph form such as one or more curves relating, for each enzyme, the said ratio between the specific activity and the initial activity to values of level of surviving microorganisms such as log reduction values. The said ratio between specific activity and initial activity is also designated by <<relative activity>> in the present application.

According to one aspect of this other advantageous embodiment of the invention, the said spectrometric measurements may in particular be carried out, for each enzymatic activity measured, at a constant temperature, in particular at 25° C., and at a constant wavelength, in particular at a wavelength of between 240 and 550 nm, for example at 340 nm. The said measurements may be recorded continuously or discontinuously over a time interval of about 30 min. In the case where higher measurement sensitivities are sought, luminometry is preferably used.

The disinfection adjusting stage of the method according to the invention may be carried out by regularly monitoring the variation of the level of surviving microorganisms (e.g. expressed as reduction, log reduction or D index) with the aid of the enzymatic indicators presented above, until the set disinfection objective is met.

The disinfection adjusting stage of the method according to the invention may also be carried out by addition of the <<disinfectant dose>> equivalent corresponding to the difference between the level of surviving microorganisms aimed at (set value) and the level of microorganisms effectively measured on the said liquid, liquid sample or concentrate at a stage of the or after disinfection.

Advantageously, the said equivalent dose of disinfectant (s) is as read on a reference curve representing the level of culturable microorganisms as a function of the dose of disinfectant(s) to which the said liquid is exposed.

The invention gives particularly advantageous results for liquids comprising microorganisms chosen from the group consisting in particular of the genus Escherichia, Alcaligenes, Bacillus, Flavobacterium, Methylobacterium, Pseudomonas, Klebsiella, Enterobacterium, Agrobacterium, Streptococcus, Micrococcus, Salmonella.

The method for regulating the disinfection of a liquid according to the invention can, in a particularly advantageous manner, be easily automated on a method for disinfecting a liquid. Unlike the prior art techniques, the method according to the invention allows a microbiological control which is reliable, rapid and easy to carry out.

Preferably, the said level of surviving microorganisms is expressed as the value of reduction (concentration of surviving microorganisms expressed in terms of the initial concentration of surviving microorganisms, as measured in the said stage 1), of log reduction ($-\log_{10}$ (reduction)) or of D index (=log reduction). The said D index also constitutes an index of the microbiological quality of the liquid considered.

The said method for regulating the disinfection of a liquid according to the invention considers, as surviving microorganisms, those of the microorganisms present which are culturable and/or those of the microorganisms present which are not culturable but which are viable. In the case where it is desired to take into account both the culturable microorganisms and the non-culturable but viable microorganisms, the said reference system then advantageously relates, for each enzyme, the said ratio between specific activity and initial activity to values of level of surviving microorganisms resulting from the addition of the values of level of culturable microorganisms and of the values of level of non-culturable but viable microorganisms, as measured with the aid of conventional techniques.

Among the said chemical or physical agents which are advantageously used for the said disinfection, there may be mentioned chlorine and its derivatives, UV radiation, ozone, $H_2O_2$, filtration membranes, temperature, ultrasound or ionizing radiation.

Other characteristics and advantages of the present invention will also emerge through the following embodiments which are given as a guide with no limitation being implied.

BRIEF DESCRIPTION OF THE FIGURES

The said examples refer to FIGS. 1, 2 and 3.

DETAILED DESCRIPTION OF THE INVENTION

EXAMPLE 1

Microbiological Control of a Water Undergoing Disinfection, Intended for Human Consumption The aim is to determine if the enzymatic activities can constitute a reliable indicator of the level of surviving microorganisms in a liquid being disinfected, such as water intended for human consumption.

Methods and results

In this regard, an inoculum is prepared by carrying out a pure culture of *Escherichia coli* (strain MG1655 available from Institut Pasteur) on nutrient medium at 25° C. (LB medium comprising 10 g/l of Bacto-tryptone, 5 g/l of Bacto-levure extract, 10 g/l of NaCl, pH adjusted to 7). The bacteria are harvested at the exponential growth phase by centrifugation and then washed with the aid of a phosphate buffer (pH 7; 0.05 M). The pellets are resuspended (about $5 \times 10^7$ cells/ml) in phosphate-buffered solutions (pH 7; 0.05 M) comprising free chlorine at various concentrations (from 0.0 to 2.0 mg/1). The various bacterial suspensions are then placed under stirring at 25° C. After 20 min, samples are collected for analyses of the samples of these bacterial suspensions (volume of 100 to 1000 ml per enzymatic activity to be measured).

For each sample, the level of surviving microorganisms and different enzymatic activities are measured in parallel according to the following methods.

Enumeration of the surviving microorganisms

For each sample of bacterial suspension, the number of microorganisms which have survived is counted, i.e. the number of culturable bacteria and/or the number of non-culturable but viable bacteria.

The enumeration of the surviving microorganisms may be carried out according to conventional techniques known to persons skilled in the art: for example, by plating on an agar medium such as TSA (tryptic soy agar, Difco) medium for the enumeration of culturable bacteria, and by the C.T.C. technique for the enumeration of non-culturable but viable bacteria (Schaule G., Flemming H. C. and Ridgway H. F. 1993, Use of 5-cyano-2,3-ditolyl tetrazolium chloride for quantifying planktonic and sessile bacteria in drinking water, Appl. Environ. Microbiol. 59:3850–3857).

From the mean number $n_i$ measured, the mean concentration ($C_i$) of surviving microorganisms at each of the doses i of free chlorine tested is then calculated. Each mean concentration $C_i$ of surviving microorganisms is then expressed relative to the maximum concentration of surviving microorganisms as measured before disinfection (maximum concentration $C_{max}$) In the case of the present illustration, $C_{max}$ corresponds to the mean concentration of surviving microorganisms as measured in the absence of free chlorine. Each $C_i$ is thus translated into a value of reduction (or of elimination) with the aid of the formula:

$$\text{reduction} = C_i/C_{max}$$

This level of surviving microorganisms $$\frac{C_i}{C_{max}}$$

also represents a measurement of the quality of disinfection.

Figure 1:
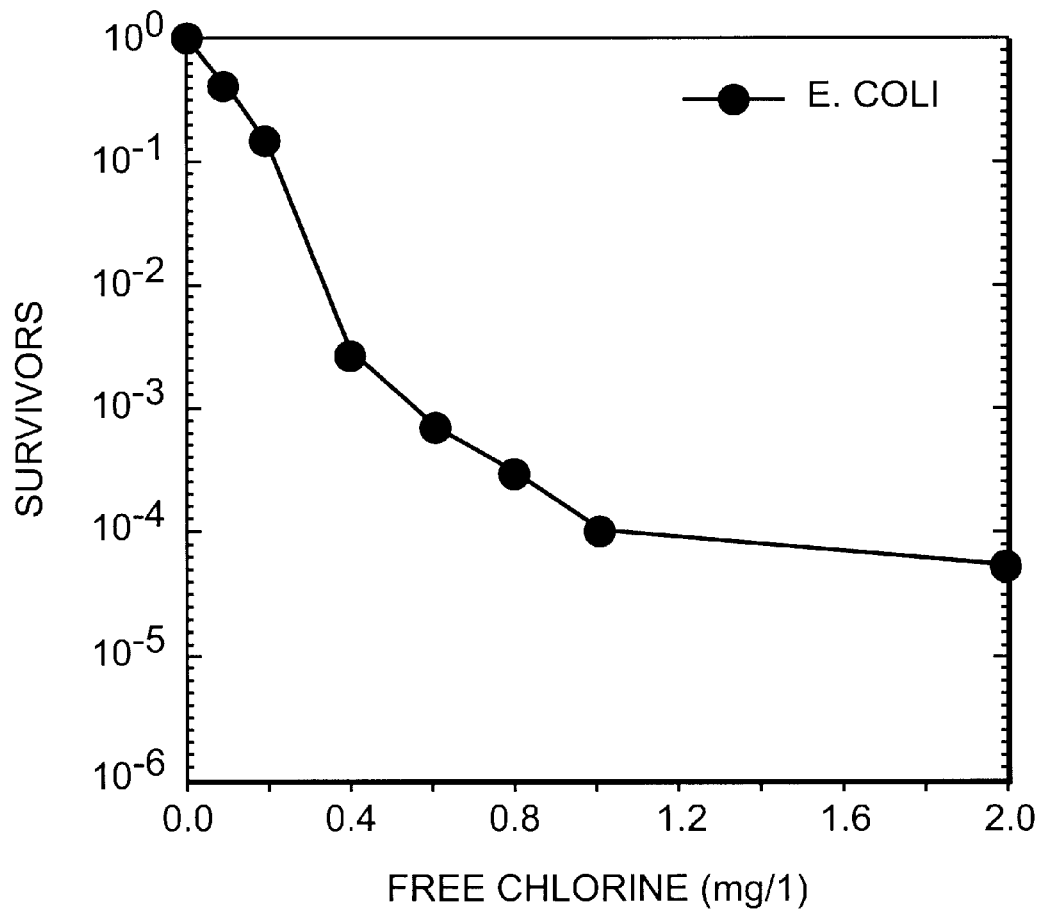
FIG. 1 represents the level of culturable *escherichia coli* bacteria (expressed as the value of reduction relative to he initial population) as a function of the applied concentration of free chlorine (mg/l)

The results of the enumerations of culturable microorganisms are illustrated by FIG. 1 where the level of culturable *E. coli* bacteria is plotted as a function of the free chlorine dose applied. The reduction (or elimination) values corresponding to the concentrations of culturable microorganisms as obtained by enumeration are plotted on the y-axis of FIG. 1, and expressed relative to the maximum concentration measured before disinfection: $10^0$ indicates a concentration of culturable microorganisms equal to the maximum concentration measured; $10^{-1}$ indicates that the concentration of culturable microorganisms has decreased by a factor of 10, $10^{-2}$ indicates that the concentration of culturable microorganisms has decreased by a factor of $10^2$, and the like. The initial concentration of free chlorine in the corresponding bacterial suspension is plotted on the x-axis of FIG. 1. The procedure is carried out in an identical manner with the results of the enumerations of non-culturable but viable microorganisms, which may, if desired, be added to the results of the enumeration of the culturable microorganisms.

Enzymatic activities

In parallel with the enumeration of the surviving microorganisms described above, various enzymatic activities are measured.

The experiments relating to two enzymes are presented here more particularly: glucose-6-phosphate dehydrogenase (designated hereinafter ZWF) and glutathion reductase. These enzymes are commonly present in many microorganisms; they are therefore capable of being able to represent the entire microbial populations present in the suspensions and thus to give the picture resulting from the disinfection carried out.

In the experiments described here, the bacteria in suspension are in concentrations which are too low for their enzymatic activities to be correctly measured directly on the liquid sample collected without prior concentration. The samples of suspensions are therefore filtered here (0.22 μm membrane) so as to recover the microorganisms therefrom. The microorganisms may also be harvested by centrifugation at 3000 g for 10 min at 40° C.

The comparative studies carried out show that it is preferable to lyse the microorganisms prior to he measurement of ZWF or glutathion reductase activities. The filters (or pellet) are therefore laced here in a system allowing the lysis of the microorganisms recovered: prior to a measurement of ZWF or glutathion reductase activity, the microorganisms are lysed preferably by an ultrasound probe (2 cycles of 30 s under ultrasound and 30 s of standing). It can be noted that, to measure the activity of enzymes other than ZWF or glutathion reductase, such as e.g. catalase or superoxide dismutase, the prior lysis of the microorganisms can be avoided by using a substrate which diffuses, such as lucigenin and hydrogen peroxide.

The various enzymatic activities may be measured according to techniques known to persons skilled in the art. Briefly, for each enzymatic activity to be measured, the microorganisms of each sample are placed in contact with a substrate chosen so that the targeted enzyme can catalyze its conversion and so that this enzymatic conversion can be easily monitored by conventional analytical techniques such as spectrocolorimetry, spectrofluorometry or luminometry, for which automation is possible.

To measure a glucose-6-phosphate dehydrogenase activity, the microorganisms of the sample are placed in contact with a substrate composed of 0.6 mM glucose-6-phosphate and of nicotinamide adenine dinucleotide phosphate in oxidized form (0.2 mM NADP) in the presence of a pH-stabilizing solution (addition of Tris buffer, pH 7.6, 10 mM $MgCl_2$). This substrate leads, in the presence of glucose-6-phosphate dehydrogenase, to the formation of nicotinamide adenine dinucleotide phosphate in reduced form (NADPH) the appearance of which can be monitored by spectrocolorimetry at the wavelength of 340 nm (Fraenkel D. G. and Levisohn S. R. 1967, Glucose and gluconate metabolism in an *Escherichia coli* mutant lacking phosphoglucose isomerase, J. Bact 93:1571–1578).

To measure a glutathion reductase activity, the microorganisms in the sample are placed in contact with a substrate composed of nicotinamide adenine dinucleotide phosphate in reduced form (0.2 mM NADPH) and of oxidized glutathion (2.5 mM glutathion disulphide GS-SG) in the presence of a pH-stabilizing solution (100 mM phosphate buffer, pH 7). Under the catalytic action of glutathion reductase, this substrate is converted to nicotinamide adenine dinucleotide phosphate in oxidized form (NADP) and to glutathion in reduced form (GSH). The disappearance of NADPH is then monitored in a spectrocolorimeter at the wavelength of 340 nm (Lopez-Barea J. and Lee C. Y. 1979, Mouse liver glutathione reductase: purification, kinetics and regulation, Eur. J. Biochem. 98:487–499).

The measurements of enzymatic activities are carried out here at an identical constant temperature (25° C.) with the aid of a PERKIN-ELMER model lambda 1 spectrophotometer.

The optical density value measured before the start of the enzymatic reaction considered serves as a <<measurement blank>>. The specific optical density values for each reaction medium are then recorded over time.

The specific enzymatic activity of the sample is then calculated in the linear portion of the curve representing the specific optical density observed after bringing the substrate into contact with the targeted enzyme (for example between 5 min and 35 min). The calculation of the slope of the curve <<specific optical density of the sample as a function of time>> in the 5–35 min time interval considered gives a value of this variation in specific optical density.

For each enzyme, the specific enzymatic activities measured at the various doses of disinfectants (quantity of substrate consumed or produced by unit of time) are each expressed as % of the initial value of activity recorded for the same enzyme, i.e. % of the value of activity measured, for the same enzyme, at the lowest dose of disinfectant: in the present illustration, the specific glucose-6-phosphate dehydrogenase (ZWF) activity and the specific glutathion reductase activity of the samples are expressed as % of the specific glucose-6-phosphate dehydrogenase (ZWF) and glutathion reductase activity, respectively, as measured for the bacterial suspensions containing no free chlorine (i.e. before disinfection). This ratio between specific enzymatic activity of the liquid at one stage of the method of disinfection (i.e. during or after disinfection) and specific enzymatic activity of this same liquid before disinfection is designated here relative enzymatic activity of the liquid at the said stage of disinfection.

The relative enzymatic activities obtained are then compared with the measurements of microbiological enumerations. The results of the enumerations of culturable microorganisms are illustrated by FIGS. 2 and 3.

Figure 2:
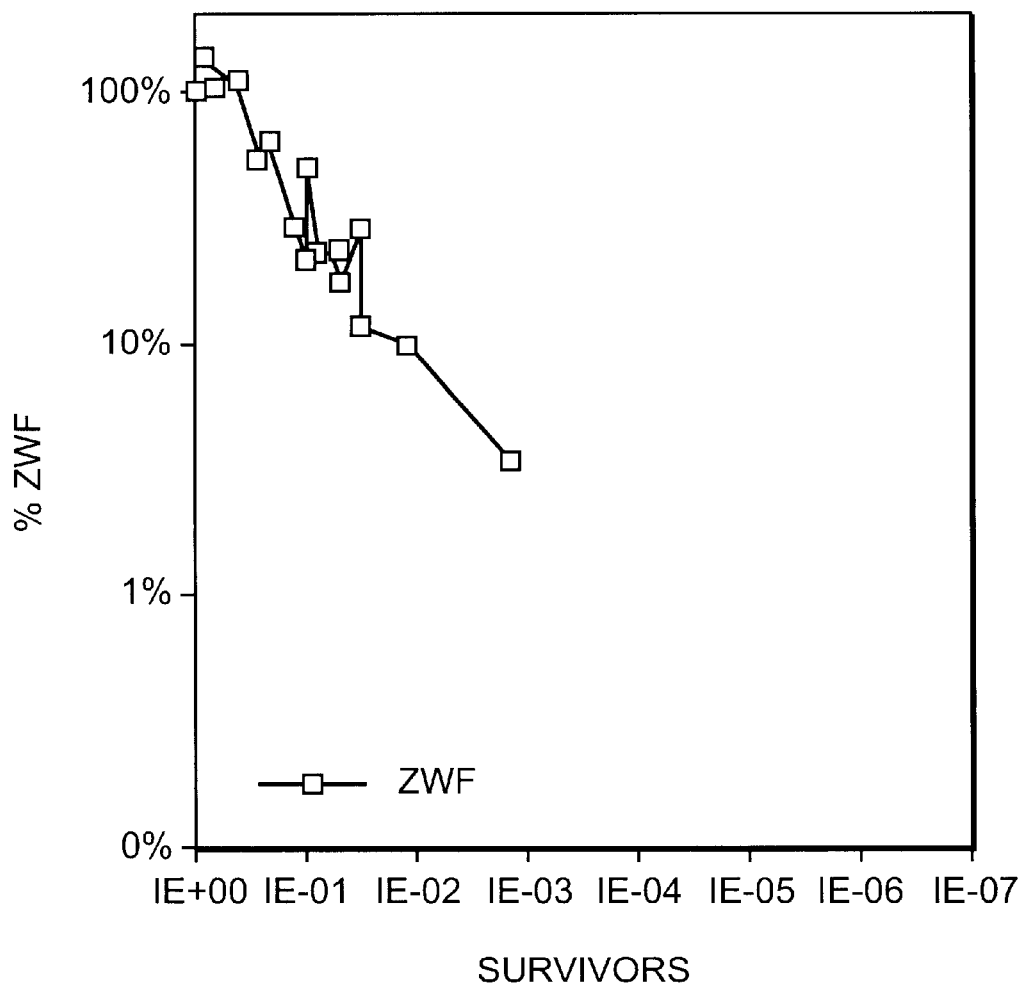
FIG. 2 represents the glucose-6-phosphate dehydrogenase (ZWF) activity, expressed as % of the maximum activity measured, as a function of the level of culturable bacteria (expressed as values of reduction relative to the initial microbial population)

FIG. 2 represents, on the y-axis, the measured glucose-6-phosphate dehydrogenase activity (ZWF), expressed as % of the maximum (initial activity) activity recorded, and, on the x-axis, the corresponding number of culturable *E. coli* obtained by enumeration.

Figure 3:
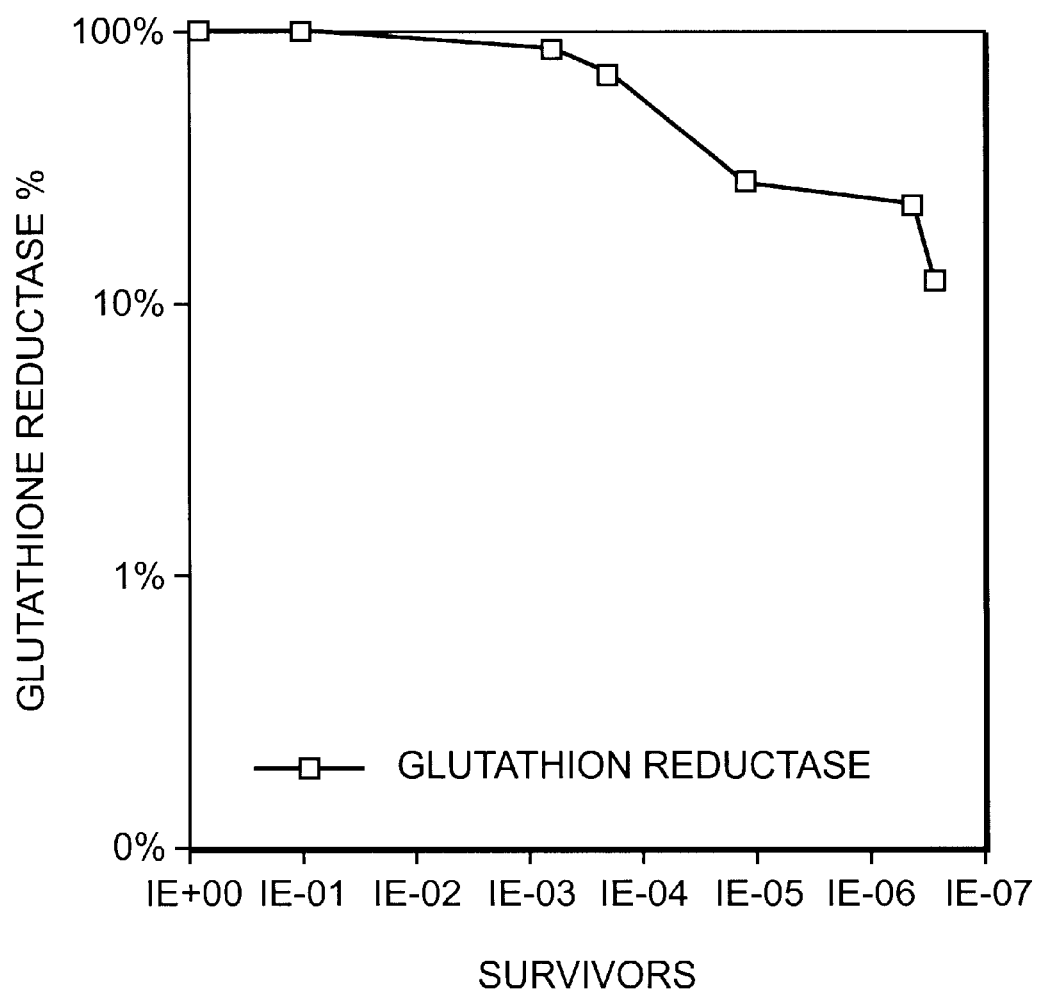
FIG. 3 represents the glutathione reductase activity, expressed as % of the initial activity (maximum) measured, as a function of the level of culturable bacteria (expressed as values of reduction relative to the maximum microbial population).

FIG. 3 represents, on the y-axis, the measured glutathion reductase activity, expressed as % of the maximum activity recorded (initial activity) and, on the x-axis, the corresponding number of culturable *E. coli* obtained by enumeration.

In FIG. 2 as well as in FIG. 3, the number of surviving microorganisms is expressed as a function of the log reduction applied according to the following formula:

$$\log \text{reduction} = -\log_{10}(C_i/C_{max})$$

where $C_i$ and $C_{max}$ are as defined above.

If necessary, the same types of figure may be obtained taking into account the results of the enumerations of non-culturable but viable microorganisms.

In FIG. 2 as well as in FIG. 3, the log reduction values are plotted on the x-axis in the following manner: 1E+00 represents a number of culturable microorganisms equal to the maximum number recorded (suspension having no free chlorine); 1E-01 represents a number of culturable microorganisms equal to the maximum recorded number decreased by a number of microorganisms corresponding to a log reduction value of 1; 1E-02 represents a number of culturable microorganisms equal to the maximum recorded number decreased by a number of microorganisms corresponding to a log reduction value of 2, and so on up to 1E-07 which represents a number of culturable microorganisms equal to the maximum recorded number decreased by a number of microorganisms corresponding to a log reduction value of 7.

It may be noted that this log reduction value also constitutes an index of the microbiological quality of the liquid considered, which index is called D.

The results obtained show that the monitoring of the glucose-6-phosphate dehydrogenase activity (relative activity) is an indicator representative of the number of surviving microorganisms for a range of samples ranging from liquid samples which have not been subjected to any treatment for the removal of microorganisms to liquid samples having a log reduction (or elimination) of less than or equal to about 3 (cf. FIG. 2).

The results obtained also show that the glutathion reductase activity (relative activity) is a representative indicator of the number of surviving microorganisms for a range of liquid samples having a log reduction (or elimination) of between 4 and 7 approximately (cf. FIG. 3). Indeed, the activity of glutathion reductase is not significantly affected before reaching 4 log reduction. A significant proportionality between relative activity and log reduction is observed, for this enzyme, only on the log reduction zone of between 4 and 7 approximately.

Similarly, we were able to demonstrate that the superoxide dismutase (relative) activity (measurements in luminometry with the aid of lucigenin) is an indicator which is representative of the number of surviving microorganisms for a range of liquid samples having a log reduction (or elimination) of between 3 and 6 approximately. The superoxide dismutases and the catalases exhibit furthermore the advantage of not requiring lysis treatment: the measurement of their activity can be carried out on a diffusive substrate such as lucigenin and hydrogen peroxide, respectively, by luminometry.

The various enzymes tested do not therefore cover the same sensitivity domains: the relative activity of glucose-6-phosphate dehydrogenase (ZWF) is an indicator which is representative of the number of surviving microorganisms (log reduction) in liquid samples which have been subjected to only small relative reductions in microbial populations, the relative activity of superoxide dismutase and of glutathion reductase are indicators which are representative of the number of surviving microorganisms (log reduction) in liquid samples which have been subjected to relative reductions in microbial populations which are moderate to high.

The same types of range of sensitivity (proportionality between relative activity and log reduction for certain zones of log reduction values) have been able to be observed by measuring the relative activity of malate dehydrogenase, glyceraldehyde-3-phosphate dehydrogenase, catalases (either by measuring the consumption of hydrogen peroxide at 240 nm in a buffered solution at pH 7 or by chemiluminescence). Persons skilled in the art will be able to find other examples of enzymes and of protocols for measuring enzymatic activities in various reference books such as: *Oxidative stress and the molecular biology of antioxidant defenses*, 1997, Cold Spring Harbor Laboratory Press 0-87969-502-1/97; Lehninger 1977, Biochimie, Flammarion ISBN 2-257-25009-5; *Methods in Enzymology*, Academic Press Inc., e.g. volumes I-XLI-XLII-89-105 and 234.

Any enzyme for which a significant proportionality (significant slope, for example less than −0.2) between relative activity and log reduction can be demonstrated, for example by following the protocol described above, constitutes a reliable indicator according to the invention.

The same types of range of enzymatic sensitivity may be obtained by applying to the *E. coli* suspensions not increasing doses of chlorine but increasing doses of ozone or increasing doses of UV.

Discussion

It therefore appears that the measurement of enzymatic activity makes it possible to monitor the variation in microbial populations in a liquid which is being disinfected. These various enzymatic indicators for microbial monitoring makes it possible to account for all of the microbial populations: culturable microorganisms and non-culturable but viable microorganisms.

It is possible, for example, to monitor the ZWF relative activity for log reduction values of less than 3, and the glutathion reductase relative activity for log reduction values greater than 4. In the case where a precise measurement of a log reduction of between 3 and 4 is required, it is then possible, for example, to measure a superoxide dismutase relative activity.

In the case where the disinfection carried out has not led to log reduction values greater than 6, it is then possible to either simply monitor the superoxide dismutase relative activity, which will start to respond only from log reduction values greater than 3, or to monitor the ZWF relative activity up to log reduction values of 3, and then the superoxide dismutase relative activity beyond.

The various types of enzymatic indicator for microbial monitoring presented above therefore make it possible to know the log reduction value for the liquid monitored, and thereby its D index of microbiological quality, its reduction value and the number of microorganisms which survive therein. They therefore give in fine a measurement of the speed and of the efficiency of the method of disinfection applied.

If the number of surviving microorganisms in the liquid monitored (e.g. expressed in the form of a log reduction or index of quality of disinfection) does not correspond to the disinfection objective set (e.g. set value of the log reduction or of quality of disinfection), the dose of disinfectant(s) applied to the said liquid (e.g. the concentration of free chlorine, of ozone, the dose of UV, of temperature, of ultrasound, of ionizing radiation) may be adjusted accordingly.

This increase or decrease in the dose of disinfectant(s) may be brought about by regularly monitoring the variation in the number of surviving microorganisms (log reduction) with the aid of the enzymatic indicators presented above and until the set disinfection objective is achieved.

The adjustment of the dose of disinfectant(s) may also be made with the aid of preestablished reference curves on a sample of the said liquid representing the level of surviving microorganisms, e.g. expressed as log reduction values, as a function of the applied dose of disinfectants) (e.g. increasing doses of free chlorine, of ozone, of UV, of temperature, ultrasound or ionizing radiation).

Such reference curves make it possible to read the values of doses of disinfectant(s) which are equivalent, respectively, to the measured level and to the desired level of surviving microorganisms as obtained with the aid of the enzymatic indicators presented above. The dose of disinfectant(s) applied to the liquid monitored then simply has to be increased or decreased by the difference read between these equivalent doses of disinfectant(s).

Such reference curves may for example be obtained by counting the surviving microorganisms in a sample of the said liquid exposed to increasing doses of disinfectant (e.g. increasing concentrations of free chlorine, of ozone, increasing doses of UV, of ionizing radiation, of ultrasound, or increasing temperature values).

The method for regulating the disinfection of a liquid according to the invention therefore makes it possible, with the aid of measurements of enzymatic activities, to completely, simply and rapidly (less than one hour) monitor the disinfection of a liquid, regardless of the physiological state or the identity of the microorganisms surviving therein. The method for regulating the disinfection of a liquid according to the present invention has, furthermore, the particular advantage of being easy to automate, unlike the methods using microscopy or microbiological cultural techniques.

It is still of course the case that the present invention is not limited to the explanatory embodiments described and represented above, but it encompasses all the variants. Accordingly, the measurements of enzymatic activities may in particular be carried out by analytical techniques other than those mentioned above.

What is claimed is:

1. A method for regulating the disinfection of a liquid, comprising the steps:
   A. at one stage of the disinfection, designated hereinafter stage 2, measuring the activity of at least one enzyme by bringing microorganisms which may be present in the liquid into contact with a substrate chosen as being capable of revealing the activity of the enzyme, this enzymatic activity being a specific activity,
   B. at one stage, designated hereinafter stage 1, prior to stage 2, measuring the activity of the same enzyme as in A, this activity being an initial activity,
   C. translating, for each enzyme, the specific activity and initial activity, into levels of microorganisms surviving in the liquid at stage 2 of the disinfection by means of a reference system preestablished with the aid of a sample of the liquid collected at stage 1 and then exposed to increasing doses of at least one disinfectant, and
   D. adjusting, as a function of the level of surviving microorganisms, the agents used for the disinfection.

2. The method according to claim 1, wherein stage 1 corresponds to a stage before disinfection of the liquid and in that stage 2 corresponds to any stage of the disinfection.

3. The method according to claim 1, wherein the liquid is a liquid intended to be in contact with humans or animals.

4. The method according to claim 1, wherein said bringing of the microorganisms which may be present in the said liquid into contact with the substrate is carried out by bringing the liquid or a sample of the liquid directly into contact with the said substrate.

5. The method according to claim 1, wherein the bringing of the microorganisms which may be present in the liquid or liquid sample into contact with the substrate is carried out by bringing a filtrate, or a centrifugation pellet, of the liquid or liquid sample, into contact with the substrate.

6. The method according to claim 1, wherein the liquid, liquid sample or concentrate are subjected, prior to said measurement of the activity of at least one enzyme, to a lysis treatment.

7. The method according to claim 1, wherein the enzyme whose activity is a measured exhibit in the liquid, liquid sample or concentrate a ratio between the specific activity and the initial activity in close relationship, and with a slope which is significantly different from zero, with the level of surviving microorganisms over at least one zone of values of the levels of surviving microorganisms.

8. The method according to claim 1, wherein the at least one enzyme whose activity is measured is a glucose-6-phosphate dehydrogenase, a malate dehydrogenase, a glyceraldehyde-3-phosphate dehydrogenase, a catalase, a superoxide dismutase or a glutathion reductase.

9. The method according to claim 1, wherein the measurements of specific activity and initial activity are made with the aid of a spectrophotometer, a spectrofluorometer or a luminometer, optionally having several channels for analysis.

10. The method according to claim 1, wherein the translation into level of surviving microorganisms with the aid of the preestablished reference system comprises for each enzyme, the calculation of the ratio between the specific activity and initial activity, expressable as a percentage.

11. The method according to claim 1, wherein the reference system exists in graph form relating, for each enzyme, the ratio between the specific activity and the initial activity to values of surviving microorganisms levels.

12. The method according to claim 9, wherein the spectrometric measurements are carried out, for each enzymatic activity measured, at a constant temperature 25° C., and at a constant wavelengths between 240 and 550 nm.

13. The method according to claim 9, wherein the spectrometric measurements are carried out continuously or discontinuously over a time interval of about 30 min.

14. The method according to claim 1, wherein the adjustment of doses of the chemical or physical agent is made by addition of a disinfectant dose equivalent corresponding to the difference between the level of surviving microorganisms aimed at and the level of microorganisms measured on the liquid, liquid sample or concentrate.

15. The method according to claim 14, wherein the equivalent dose of disinfectant is as read on a reference curve representing the level of surviving microorganisms as a function of the dose of disinfectant to which the liquid is exposed.

16. The method according to claim 1, wherein the liquid comprises microorganisms chosen from the group consisting of the genus Escherichia, Alcaligenes, Bacillus, Flavobacterium, Methylobacterium, Pseudomonas, Klebsiella, Enterobacterium, Agrobacterium, Streptococcus, Micrococcus, Salmonella.

17. The method according to claim 1, wherein disinfecting a liquid occurs automatically.

18. The method according to claim 1, wherein the level of surviving microorganisms is expressed as the value of reduction concentration of surviving microorganisms expressed in terms of the initial concentration of surviving microorganisms, as measured in stage 1, of log reduction ($-\log_{10}$ (reduction) or of D index (=log reduction).

19. The method according to claim 1, wherein the surviving microorganisms are culturable microorganisms and/or non-culturable but viable microorganisms.

20. The method according to claim 1, wherein the agents which are used for the disinfection, are chosen from the group consisting of chlorine and its derivatives, UV radiation, ozone, $H_2O_2$, filtration membranes, temperature, ultrasound or ionizing radiation.

* * * * *